(12) United States Patent
Gorospe et al.

(10) Patent No.: US 8,910,501 B2
(45) Date of Patent: Dec. 16, 2014

(54) WINDING MANDREL FOR VASOOCCLUSIVE COILS

(71) Applicant: DePuy Synthes Products, LLC, Raynham, MA (US)

(72) Inventors: Marcelino Gorospe, Redwood City, CA (US); Edsel San Diego, San Jose, CA (US); Thu Anh Ho, San Jose, CA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 14/047,692

(22) Filed: Oct. 7, 2013

(65) Prior Publication Data

US 2014/0034769 A1 Feb. 6, 2014

Related U.S. Application Data

(62) Division of application No. 12/025,672, filed on Feb. 4, 2008, now abandoned.

(60) Provisional application No. 60/899,967, filed on Feb. 7, 2007.

(51) Int. Cl.
*B21F 3/06* (2006.01)
*B21C 47/00* (2006.01)
*B21F 45/00* (2006.01)
*A61B 17/12* (2006.01)
*A61B 17/00* (2006.01)

(52) U.S. Cl.
CPC ............... *B21C 47/00* (2013.01); *B21F 45/008* (2013.01); *A61B 17/12022* (2013.01); *A61B 17/12109* (2013.01); *A61B 17/12145* (2013.01); *A61B 2017/00526* (2013.01); *A61B 2017/00867* (2013.01)
USPC ............... 72/141; 72/137; 140/71 C; 140/124

(58) Field of Classification Search
CPC .. B21F 45/00; B21F 45/008; A61B 17/12022
USPC ....... 140/71 C, 102.5, 103, 123, 124; 72/135, 72/137, 141, 371, 466.2; 242/590, 360
See application file for complete search history.

(56) References Cited

U.S. PATENT DOCUMENTS 5,624,461 A 4/1997 Mariant
5,649,949 A 7/1997 Wallace et al.
(Continued)

FOREIGN PATENT DOCUMENTS

DE 3203410 A1 11/1982
EP 0747014 A1 12/1996
(Continued)

OTHER PUBLICATIONS

Chinese Application No. 201210035230.2 Office Action dated Apr. 30, 2014.

*Primary Examiner* — Debra Sullivan

(57) ABSTRACT

The winding mandrel includes a pair of generally rounded-cube shaped or orthogonally flat-sided spherical main bodies connected together and having a plurality of cylindrical posts for forming vasoocclusive coils. The main bodies are connected together by a transition post, and the posts of the two main bodies are typically offset. A front end post and back end post are disposed on the front and rear ends of the mandrel. A short winding post member may be added between the connections of the two main bodies to provide additional winding posts.

7 Claims, 2 Drawing Sheets

(56) References Cited

U.S. PATENT DOCUMENTS

| | | | |
|---|---|---|---|
| 5,911,731 A | 6/1999 | Pham et al. | |
| 6,231,586 B1 * | 5/2001 | Mariant | 606/191 |
| 6,322,576 B1 | 11/2001 | Wallace | |
| 6,638,291 B1 | 10/2003 | Ferrera et al. | |
| 2002/0019647 A1 * | 2/2002 | Wallace et al. | 606/200 |

FOREIGN PATENT DOCUMENTS

| | | |
|---|---|---|
| EP | 0765636 A2 | 4/1997 |
| WO | 9909893 | 3/1999 |
| WO | 0012016 | 3/2000 |
| WO | 0193937 | 12/2001 |

* cited by examiner

WINDING MANDREL FOR VASOOCCLUSIVE COILS

CROSS-REFERENCES TO RELATED APPLICATIONS

This application is a divisional of U.S. Ser. No. 12/025,672, filed on Feb. 4, 2008, which is based on and claims priority to Provisional Application No. 60/899,967, filed Feb. 7, 2007.

BACKGROUND OF THE INVENTION

This invention relates generally to vasoocclusive devices, and more particularly concerns a mandrel for forming at least a portion of a vasoocclusive coil in a three dimensional configuration by winding of the coil about one or more portions of the mandrel.

Vasoocclusion devices are therapeutic devices that are placed within the vasculature of the human body, typically via a catheter, either to block the flow of blood through a vessel making up that portion of the vasculature through the formation of an embolus, or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. For example, the vasoocclusive device may include one or more vasoocclusive members wound to form a generally spherical or ovoid shape in a relaxed state. Vasoocclusive members can be wound around an appropriately shaped mandrel or form and then heat-treated to retain the shape after removal from the heating form.

One type of mandrel used for winding and forming a vasoocclusive coil around the surface of the mandrel has a substantially spherical main body with six cylindrical posts having a diameter slightly smaller than that of the main body, disposed on the body and aligned with the three orthogonal x, y and z axes through the body of the mandrel, for aligning and shaping one or more portions of the vasoocclusive device as it is wound on the mandrel. One of the posts is longer than the other posts, to serve as a mandrel for helically winding a proximal portion of the vasoocclusive coil. In one variation of the mandrel, the mandrel has a main body that is substantially cubical, with six cylindrical posts disposed on each of the faces of the main body, and one of the posts being longer than the others.

Another type of mandrel has a substantially orthogonal main body with six cylindrical posts having a diameter slightly smaller than that of the main body, disposed on the body and aligned with the three orthogonal x, y and z axes through the body of the mandrel, for aligning and shaping the distal portion of the vasoocclusive device as it is wound on the mandrel. Preferably one of the posts is longer than the other posts, to serve as a mandrel for helically winding the proximal portion of the vasoocclusive coil. The mandrel may include a threaded aperture in a face of one of the posts and coaxially aligned with the orthogonal axis the post for receiving a corresponding end of a generally cylindrical handle, which is correspondingly threaded, and the handle can also be used as a mandrel for winding a portion of the vasoocclusive coil with a helical shape.

Another type of mandrel has a substantially spherical main body, with a plurality of circumferential grooves defined on the surface of the main body, and this type of mandrel may additionally have a plurality of posts mounted on the main body of the mandrel for aligning the occlusive device as it is wound on the mandrel. The surface of the mandrel may also have one or more apertures for receiving one or more ends of the strands, to assist winding into the desired form.

Heat treatment of the wound coil at a temperature of about 1100° F. for approximately four hours or more is typically sufficient to impart the form to the occlusive device when the shape memory material is a nickel titanium super-elastic alloy. After the heat treatment, the occlusive device is removed from the mandrel, and cold worked into the desired collapsed elongated configuration for placement into a catheter or cannula for use. When the occlusive device reaches its destination in the vasculature during vascular therapy, it assumes the primary shape imparted from the heat treatment on the mandrel.

Such spherical, cubical or orthogonal mandrels for winding of vasoocclusive coils have proved suitable for winding coils in such shapes, and allow for the combination of multiple coils or the winding of various shapes in an individual coil, but it would be desirable to provide a winding mandrel offering a greater variety of options for winding patterns for forming other shapes of vasoocclusive coils, such as for forming longer framing coils, and for providing shorter transitions between coils for coils with more than six loops, for example. The present invention satisfies these and other needs.

SUMMARY OF THE INVENTION

Briefly, and in general terms, the invention provides for a winding mandrel having a pair of generally rounded-cube shaped or orthogonally flat-sided spherical main bodies connected together, and each having a plurality of cylindrical posts, to provide from ten to twelve available winding posts, allowing for a greater variety of options for winding patterns for forming other shapes of vasoocclusive coils, as well as short transitions between portions of coils wound on the mandrel.

The present invention accordingly provides for a winding mandrel having a pair of generally rounded-cube shaped or orthogonally flat-sided spherical main bodies, each having a plurality of cylindrical posts disposed on the bodies and aligned with orthogonal x and y axes through the bodies of the mandrel, for aligning and shaping one or more portions of the vasoocclusive device as it is wound on the mandrel. In a presently preferred embodiment, the cylindrical posts are attached to flat sides of the main bodies. In a presently preferred embodiment, the orthogonal x and y axes through the main bodies of the mandrel are offset with respect to each other. The cylindrical posts typically have a diameter slightly smaller than that of the main bodies. The main bodies are connected together by a central transition post extending between the main bodies along a longitudinal central z axis through the main bodies. A front end cylindrical post and a back end cylindrical post are disposed on front and rear ends of the main bodies extending along the longitudinal central z axis through the main bodies, providing for a total of ten winding posts. One of the front end and back end cylindrical posts may be substantially elongated with respect to the other, to provide a handle, or to serve as a post for helically winding an elongated portion of a vasoocclusive coil.

In another embodiment, a short winding post is added between the connections of the two main bodies for two additional winding posts.

Other features and advantages of the present invention will become more apparent from the following detailed description of the preferred embodiments in conjunction with the accompanying drawings, which illustrate, by way of example, the operation of the invention.

DETAILED DESCRIPTION OF THE PREFERRED EMBODIMENTS

Figure 1:
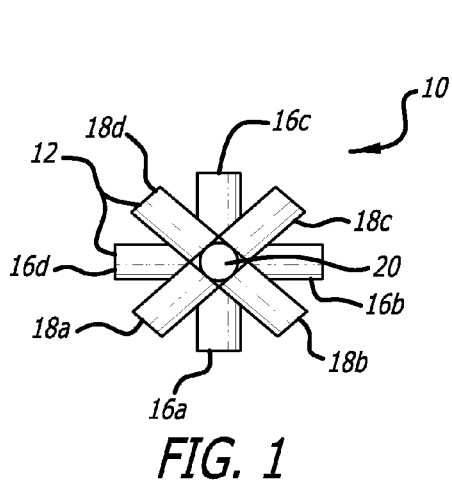
FIG. 1 is a rear elevational view of a first embodiment of a winding mandrel according to the present invention.

Referring to the drawings, which are provided for purposes of illustration and by way of example, the present invention provides for a winding mandrel for forming at least a portion of a vasoocclusive coil in a three-dimensional configuration by winding of the coil about one or more portions of the mandrel.

Figure 2:
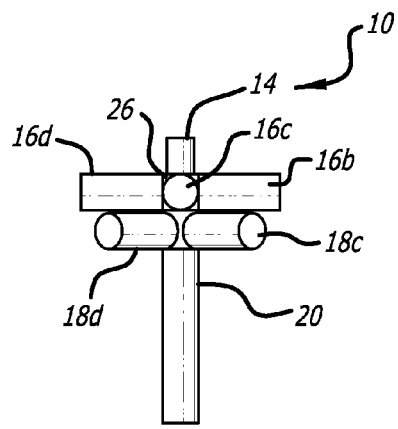
FIG. 2 is a top plan view of the winding mandrel of FIG. 1.
Figure 3:
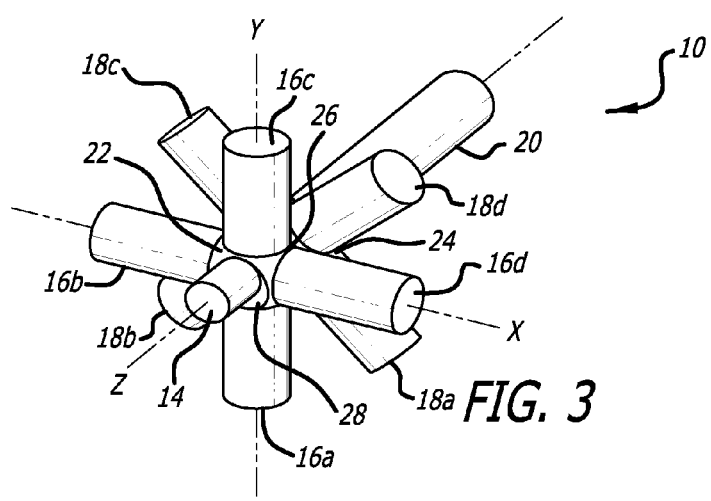
FIG. 3 is a perspective view of the winding mandrel of FIG. 1.

As is illustrated in FIGS. 1-3, in a first embodiment, the mandrel 10 includes ten winding posts 12 (one front post 14, four primary winding posts 16a, b, c, d, four secondary winding posts 18a, b, c, d, and one back post 20) and two generally rounded-cube shaped or orthogonally flat-sided spherical main bodies 22, 24, with a transition post 26 between the two main bodies. Each main body is machined on six sides to provide flat sides 28 for connecting to the winding posts and the other main body. The front winding post may be smaller in diameter than the diameter of the other posts, and is typically approximately 75% the size of the other posts. This front winding post is connected to one of the machined flat sides and may be generally tangent to the main body 22 as the starter for the first coil loop.

The four primary winding posts are connected to the other four flat sides perpendicular to the front winding post. These posts form a cross pattern perpendicular to the front winding post.

The second main body 24 is connected at the last machined flat spot of the first main body. Four secondary winding posts and a back post are connected at the machine flat sides of the second main body. The four secondary winding posts will form a similar pattern as the primary winding posts, except that they are preferably indexed over or offset (such as approximately 45 degrees, for example), so that the individual secondary posts line up between the primary winding posts. The back winding post is mounted on the end opposite to the front winding post, and in line with the front winding post, and is longer to serve as a handle for holding the mandrel during the winding process, or to serve as a post for helically winding an elongated portion of a vasoocclusive coil.

Figure 4:
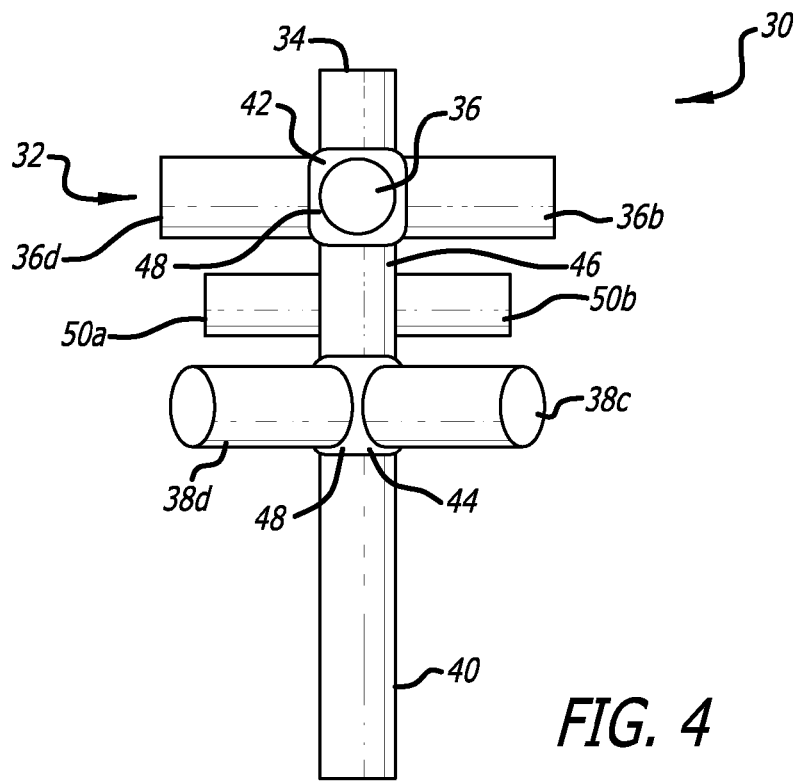
FIG. 4 is a top plan view of a second embodiment of a winding mandrel according to the present invention.
Figure 5:
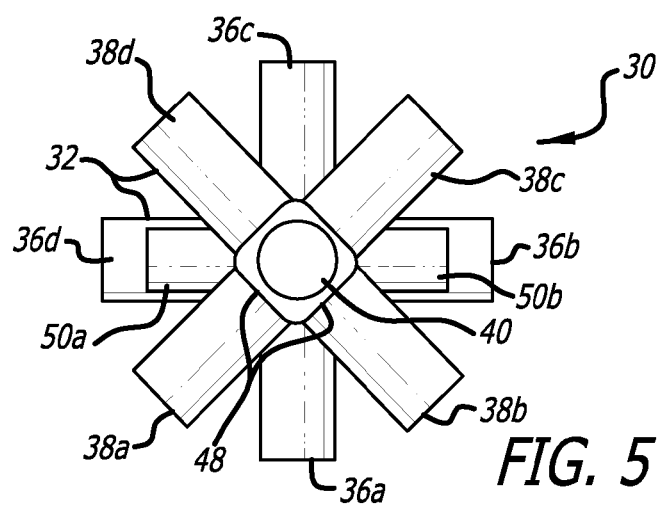
FIG. 5 is a rear elevational view of the winding mandrel of FIG. 4.

In a second embodiment, a twelve post winding mandrel is substantially the same as the ten post winding mandrel of FIGS. 1-3, except that a short winding post is added between the connections of the two generally rounded-cube shaped or orthogonally flat-sided spherical main bodies for two additional winding posts. Referring to FIGS. 4 and 5, in the second embodiment, the mandrel 30 includes winding posts 32 (one front post 34, four primary winding posts 36a, b, c, d, four secondary winding posts 38a, b, c, d, and one back post 40) and two generally rounded-cube shaped or orthogonally flat-sided spherical main bodies 42, 44, with a transition post 46 between the two main bodies. Each main body is machined on six sides to provide flat sides 48 for connecting to the winding posts and the other main body. The front winding post may be smaller in diameter than the diameter of the other posts, and is typically approximately 75% the size of the other posts. This front winding post is connected to one of the machined flat sides and may be generally tangent to the main body 42 as the starter for the first coil loop.

The four primary winding posts are connected to the other four flat sides perpendicular to the front winding post. These posts form a cross pattern perpendicular to the front winding post.

The first and second main bodies are connected by the transition post 46 between the two main bodies. Four secondary winding posts and a back post are connected at the machine flat sides of the second main body. The four secondary winding posts form a similar pattern as the primary winding posts, except that they are preferably indexed over or offset (such as approximately 45 degrees, for example), so that the individual secondary posts line up between the primary winding posts. The back winding post is mounted on the end opposite to the front winding post, and in line with the front winding post, and is longer to serve as a handle for holding the mandrel during the winding process, or to serve as a post for helically winding an elongated portion of a vasooc-clusive coil. Two additional winding posts 50a, 50b are mounted to the transition post 46, extending perpendicularly from the longitudinal axis of the transition post, between the two main bodies, to provide for a twelve post winding mandrel.

It will be apparent from the foregoing that, while particular forms of the invention have been illustrated and described, various modifications can be made without departing from the spirit and scope of the invention. Accordingly, it is not intended that the invention be limited, except as by the appended claims.

The invention claimed is:

1. A winding mandrel for forming at least a portion of a vasoocclusive coil, comprising:
   first and second spherical main bodies each having a plurality of flat sides, each of said first and second spherical main bodies having a plurality of cylindrical posts disposed on the first and second spherical main bodies, the plurality of cylindrical posts disposed on the first main body being aligned with orthogonal x and y axes through the first main body, and the plurality of cylindrical posts disposed on the second main body being aligned with orthogonal x and y axes through the second main body, wherein said first and second spherical main bodies are configured to be angularly offset with respect to each other;
   a central transition post extending between and connecting said first and second main bodies:
   at least one central cylindrical winding post connected to and extending perpendicularly from said central transition post;
   a front end cylindrical post disposed on one of said first and second spherical main bodies; and
   a back end cylindrical post disposed on the other of said first and second spherical main bodies.

2. The winding mandrel of claim 1, wherein one of said plurality of flat sides of said first main body is connected to one of said plurality of flat sides of said second main body, and said cylindrical posts are attached to remaining ones of said plurality of flat sides, respectively.

3. The winding mandrel of claim 1, wherein said plurality of cylindrical posts of said first and second spherical main bodies are angularly offset with respect to each other.

4. The winding mandrel of claim 1, wherein said cylindrical posts have a diameter slightly smaller than a diameter of the main bodies.

5. The winding mandrel of claim 1, wherein said one of the front end and back end cylindrical posts is substantially elongated with respect to the other.

6. The winding mandrel of Claim 1, wherein said first and second main bodies each have four cylindrical posts disposed on the first and second main bodies, and said cylindrical posts are attached to said flat sides, respectively, and said cylindrical posts of said first and second main bodies are angularly offset with respect to each other.

7. The winding mandrel of Claim 1, wherein said at least one central cylindrical winding post comprises first and second central cylindrical winding posts connected to and extending perpendicularly from said central transition post.

* * * * *